United States Patent
Akingba

(10) Patent No.: US 10,687,833 B2
(45) Date of Patent: Jun. 23, 2020

(54) ULTRASOUND CATHETER

(71) Applicant: Indiana University Research & Technology Corporation, Indianapolis, IN (US)

(72) Inventor: A. George Akingba, Carmel, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 287 days.

(21) Appl. No.: 15/553,833

(22) PCT Filed: Mar. 4, 2016

(86) PCT No.: PCT/US2016/020866
§ 371 (c)(1),
(2) Date: Aug. 25, 2017

(87) PCT Pub. No.: WO2016/141281
PCT Pub. Date: Sep. 9, 2016

(65) Prior Publication Data
US 2018/0070966 A1    Mar. 15, 2018

Related U.S. Application Data

(60) Provisional application No. 62/128,395, filed on Mar. 4, 2015.

(51) Int. Cl.
*A61B 17/22*     (2006.01)
*A61B 8/12*      (2006.01)
(Continued)

(52) U.S. Cl.
CPC ........ *A61B 17/2202* (2013.01); *A61B 8/0891* (2013.01); *A61B 8/12* (2013.01);
(Continued)

(58) Field of Classification Search
CPC combination set(s) only.
See application file for complete search history.

(56) References Cited

U.S. PATENT DOCUMENTS 5,131,395 A  *  7/1992  Gehlbach ............. A61B 8/0833
                                                    600/461
5,324,255 A     6/1994  Passafaro et al.
(Continued)

OTHER PUBLICATIONS

International Search Report and Written Opinion for International Application No. PCT/US2016/020866 dated May 19, 2016, 18 pages.

*Primary Examiner* — Rochelle D Turchen
(74) *Attorney, Agent, or Firm* — Barnes & Thornburg LLP

(57) ABSTRACT

A system and a method for disrupting an occlusion within a blood vessel is provided The system includes an elongated catheter body having a proximal portion, a distal portion, and a first lumen. The system further includes an ultrasound transmitter extending longitudinally through the first lumen of the catheter body and having a proximal end and a distal end. The system further includes a positioning mechanism located at a distal end of the catheter body. The positioning mechanism has a first retracted position and a second deployed position, and the positioning mechanism is radially expandable from the first retracted position to the second deployed position to position the catheter in the blood vessel.

17 Claims, 4 Drawing Sheets

(51) Int. Cl.
*A61B 8/08* (2006.01)
*A61M 25/04* (2006.01)
*A61B 17/32* (2006.01)

(52) U.S. Cl.
CPC ....... *A61B 17/22012* (2013.01); *A61M 25/04* (2013.01); *A61B 2017/22014* (2013.01); *A61B 2017/22068* (2013.01); *A61B 2017/22077* (2013.01); *A61B 2017/320064* (2013.01)

(56) References Cited

U.S. PATENT DOCUMENTS

| | | | |
|---|---|---|---|
| 5,385,148 A | | 1/1995 | Lesh et al. |
| 5,427,118 A | * | 6/1995 | Nita ................. A61B 17/22012 |
| | | | 600/585 |
| 5,484,416 A | * | 1/1996 | Gittings ............... A61B 8/0833 |
| | | | 604/164.08 |
| 8,062,566 B2 | | 11/2011 | Nita et al. |
| 8,152,758 B2 | | 4/2012 | Chan et al. |
| 8,388,573 B1 | | 3/2013 | Cox |
| 2008/0194939 A1 | | 8/2008 | Dickinson et al. |
| 2009/0306691 A1 | * | 12/2009 | Cambronne ..... A61B 17/22012 |
| | | | 606/159 |
| 2011/0082396 A1 | | 4/2011 | Wallace |

* cited by examiner

ULTRASOUND CATHETER

CROSS-REFERENCES TO RELATED APPLICATIONS

This application represents the U.S. National Stage of International Application No. PCT/US2016/020866, filed Mar. 4, 2016 which claims priority from U.S. Patent Application No. 62/128,395 filed Mar. 4, 2015.

STATEMENT REGARDING FEDERALLY SPONSORED RESEARCH

Not Applicable.

BACKGROUND OF THE INVENTION

The present invention relates generally to medical devices and methods. More specifically, the present invention relates to ultrasound catheter devices and methods for treating occlusive intravascular lesions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. Various ultrasonic catheter devices have been developed for use in ablating or otherwise removing obstructive material from blood vessels.

It would be desirable to have a system and method to provide for improved positioning and occlusion ablation capabilities. Such a system may prevent damage to the blood vessel when operating the catheter.

SUMMARY OF THE INVENTION

The present invention provides a system and method for positioning an ultrasound catheter used to disrupt an occlusion within a blood vessel.

In one aspect, an ultrasound catheter system for disrupting an occlusion within a blood vessel which can be guided from an access site on a subject's body to a target site adjacent to the occlusion is provided. The ultrasound catheter system includes an elongated catheter body having a proximal portion, a distal portion, and a first lumen, an ultrasound transmitter extending longitudinally through the first lumen of the catheter body and having a proximal end and a distal end, and a positioning mechanism located at a distal end of the catheter body. The positioning mechanism has a first retracted position and a second deployed position, and the positioning mechanism is radially expandable from the first retracted position to the second deployed position to position the catheter in the blood vessel. Preferably, the positioning mechanism centers the catheter in the blood vessel.

In the ultrasound catheter system, the positioning mechanism may comprise a balloon. An inflation lumen having an outlet may be in fluid communication with an interior space of the balloon, wherein the inflation lumen is configured to provide a fluid from the proximal end of the inflation lumen to the interior space of the balloon, and wherein the balloon moves from the retracted position to the deployed position when the fluid enters the interior space of the balloon. The positioning mechanism may further comprise a cage surrounding the balloon.

In the ultrasound catheter system, the positioning mechanism may comprise a self-expanding cage. A sheath may be configured to removably cover the cage, and the cage moves from the retracted position to the deployed position when the sheath uncovers the cage.

The ultrasound catheter system may further comprise a pilot needle configured to create a pilot hole within the occlusion. The pilot needle may be disposed within the ultrasound transmitter, and the distal head of the ultrasound transmitter may be open to the biological environment, and the pilot needle can traverse beyond the distal head of the ultrasound transmitter.

In an additional aspect, an ultrasound catheter system for disrupting an occlusion within a blood vessel which can be guided from an access site on a subject's body to a target site adjacent to the occlusion is disclosed. The ultrasound catheter system includes an elongate catheter body having a proximal portion, a distal portion, and a first lumen, an ultrasound transmitter extending longitudinally through the first lumen of the catheter body and having a proximal end and a distal end, and a pilot needle configured to create a pilot hole within the occlusion.

In the ultrasound catheter system, the ultrasound transmitter may be hollow, and the pilot needle may extend longitudinally through the ultrasound transmitter. Alternatively, the pilot needle may be hollow, and the ultrasound transmitter extends longitudinally through the pilot needle. The pilot needle may be disposed within a second lumen of the catheter body. The pilot needle may have an outside diameter of 0.010 inches to 0.040 inches.

The ultrasound catheter system may further comprise a positioning mechanism located at a distal end of the catheter body, and the positioning mechanism has a first retracted position and a second deployed position. The positioning mechanism is radially expandable from the first retracted position to the second deployed position to position the catheter in the blood vessel.

In the ultrasound catheter system, the positioning mechanism may comprise a self-expanding cage. In the ultrasound catheter system, the positioning mechanism may comprise a balloon.

In an additional aspect, a method for disrupting an occlusion within a blood vessel is provided. The method includes the steps of: guiding an ultrasound catheter system from an access site on a subject's body to a target site adjacent to the occlusion, radially expanding a positioning mechanism from the first retracted position to the second deployed position to position the catheter in the blood vessel, contacting the occlusion with the distal end of the ultrasound transmitter, and applying ultrasonic energy to the ultrasound transmitter to disrupt the occlusion.

In the ultrasound catheter system used in the method, the positioning mechanism may comprise a balloon. The ultrasound catheter system may further comprise an inflation lumen having an outlet in fluid communication with an interior space of the balloon. The inflation lumen is configured to provide a fluid from the proximal end of the inflation lumen to the interior space of the balloon; and the balloon moves from the retracted position to the deployed position when the fluid enters the interior space of the balloon. The positioning mechanism may further comprise a cage surrounding the balloon.

In the ultrasound catheter system used in the method, the positioning mechanism comprises a self-expanding cage. The ultrasound catheter system may further comprise a sheath configured to removably cover the cage, and the cage moves from the retracted position to the deployed position when the sheath uncovers the cage.

The method may further comprise creating a pilot hole within the occlusion using a pilot needle. In the method, a tip of the ultrasound transmitter is located at a center of the blood vessel when the positioning mechanism is in the second deployed position.

In another aspect, an alternative method for disrupting an occlusion within a blood vessel is disclosed. The method includes the steps of: guiding an ultrasound catheter system from an access site on a subject's body to a target site adjacent to the occlusion, creating a pilot hole within the occlusion using the pilot needle, contacting the pilot hole within the occlusion with the distal end of the ultrasound transmitter, and applying ultrasonic energy to the ultrasound transmitter to disrupt the occlusion.

In the ultrasound catheter system used in the method, the ultrasound transmitter may be hollow, and the pilot needle extends longitudinally through the ultrasound transmitter. In the ultrasound catheter system used in the method, the pilot needle may be hollow, and the ultrasound transmitter extends longitudinally through the pilot needle. In the ultrasound catheter system used in the method, the pilot needle may e disposed within a second lumen of the catheter body.

The method may comprise radially expanding a positioning mechanism of the ultrasound catheter system from a first retracted position to a second deployed position to position the catheter in the blood vessel before creating the pilot hole within the occlusion using the pilot needle. The catheter may be positioned in the blood vessel such that a tip of the ultrasound transmitter is located at a center of the blood vessel.

In the ultrasound catheter system used in the method, the positioning mechanism may comprise a self-expanding cage.

In the ultrasound catheter system used in the method, the positioning mechanism may comprise a balloon.

A device of the present disclosure centers the ultrasonic tip (approximately) in the middle of the ("angled" or "non-angled") atherosclerotic plaque, therefore allowing for central lumen drilling of occluded blood vessels.

A device of the present disclosure prevents a tip of an ultrasonic catheter from veering into a side-branch or into the subintimal space of the blood vessel. The self-centering capabilities of the catheter is achieved by contacting the circular side-wall of the healthy portion of the blood vessel, thereby allowing the ultrasonic catheter tip to be located at the center of the blood vessel. The ultrasonic tip is then activated such that it is able to drill through any angled occlusive plaque. An additional sharp prosthetic (e.g., metal) pilot needle may be used to bore through a tough section of plaque that the ultrasonic tip is unable to drill through.

Various other features of the present invention will be made apparent from the following detailed description and the drawings.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
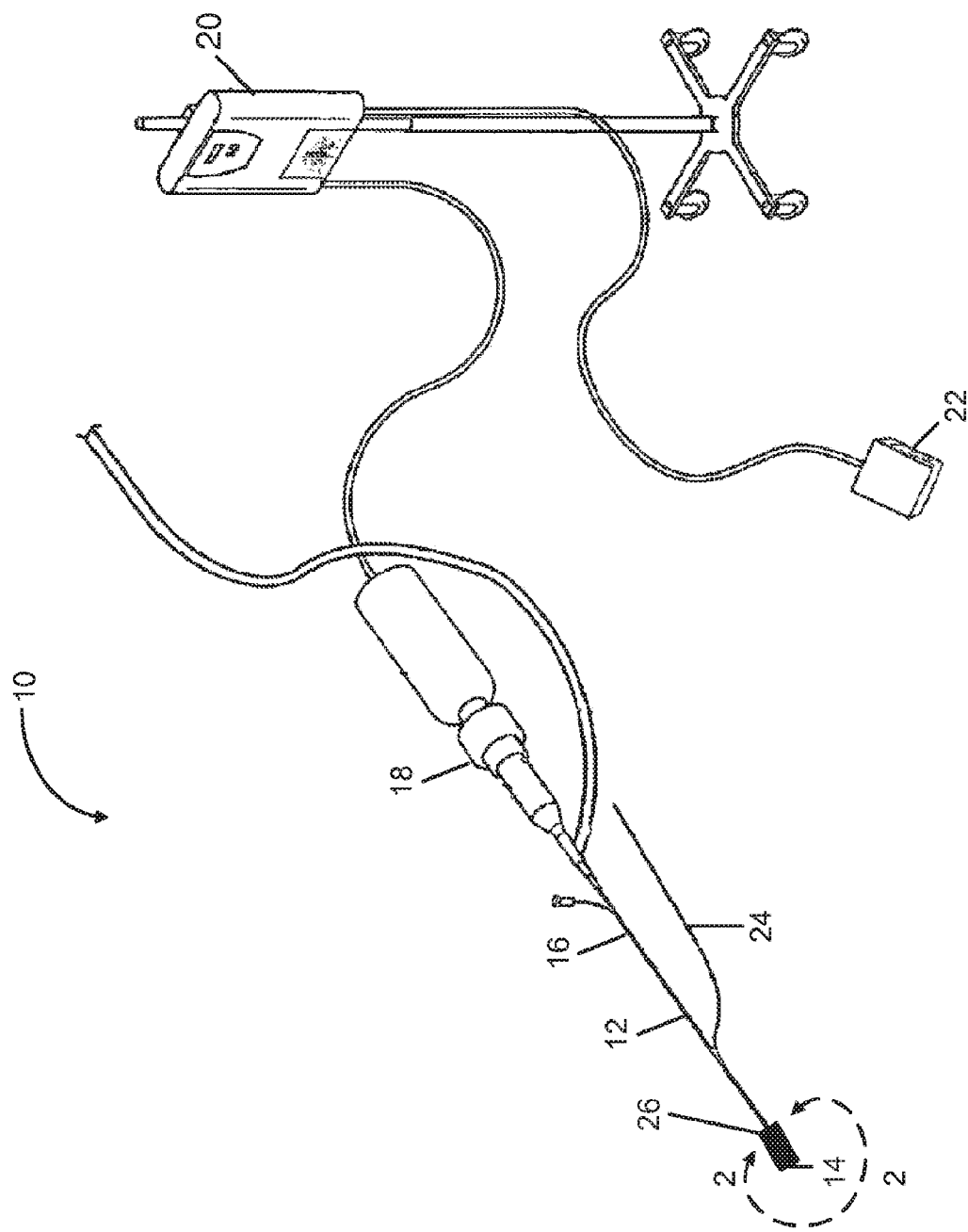
FIG. 1 is a schematic of an example ultrasound catheter system in accordance with the present disclosure.

Referring to FIG. 1, an ultrasound catheter system 10 is shown. The ultrasound catheter system 10 includes a catheter body 12, the catheter body having a distal end 14 and a proximal end 16. Generally, the ultrasound catheter system 10 includes one of the ultrasound transmitters 160, 260, 360, which can be seen in FIGS. 7-9. The ultrasound catheter system 10 further includes an ultrasound transducer 18, and an ultrasound generator 20 coupled with the transducer. A foot-actuated on/off switch 22 may be included to provide ultrasonic energy to the ultrasound transducer 18 and, thus, to the ultrasound transmitter. It is also possible for the ultrasound catheter system 10 to include a pilot needle 24 (or its various alternative embodiments 124, 224, 324 of FIGS. 7-9). In a further embodiment, the ultrasound catheter system 10 may include a positioning mechanism 26 located at the distal end 14 of catheter body 12. It is possible for the positioning mechanism 26 to be a balloon, a balloon and cage, or a self-expending cage.

Figure 2:
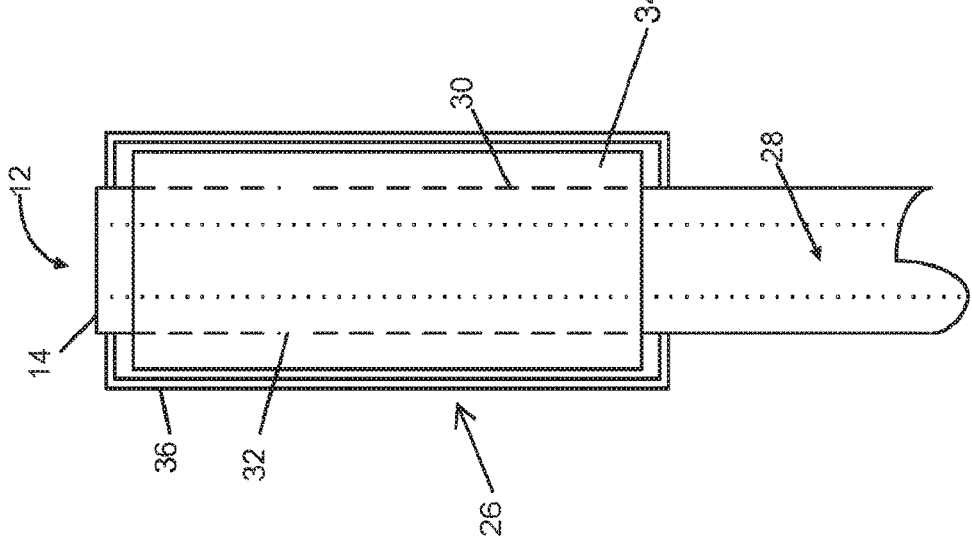
FIG. 2 is a detailed side view, taken along line 2-2 of FIG. 1, of the balloon and cage positioning mechanism of the catheter system of FIG. 1 in a retracted position.

One example embodiment of the catheter body 12 having a positioning mechanism 26 in a retracted position can be seen in FIG. 2. The catheter body 12 includes a lumen 28 configured to receive an elongated object, for example, the ultrasound transmitter or the pilot needle 24. The catheter body 12 further includes an inflation lumen 30. The inflation lumen 30 includes an outlet 32 configured to provide fluid from a fluid source via the inflation lumen 30 to a balloon 34, which may be radially expandable. An optional cage 36 may surround the balloon 34 to provide support to the balloon 34. The cage 36 may comprise a flexible metallic or polymeric material.

Figure 4:
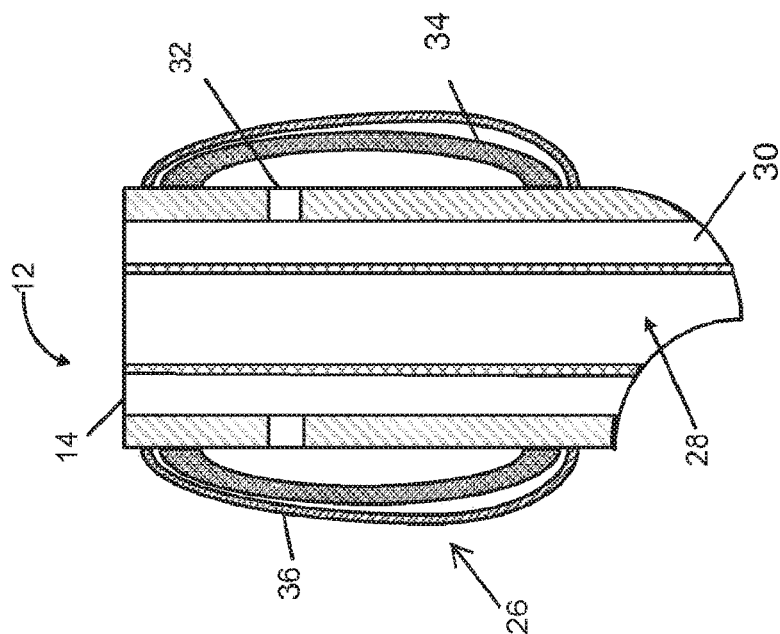
FIG. 4 is a cross-sectional view, taken along line 4-4 of FIG. 3, of the balloon and cage positioning mechanism of the catheter system of FIG. 1 in a deployed position.
Figure 3:
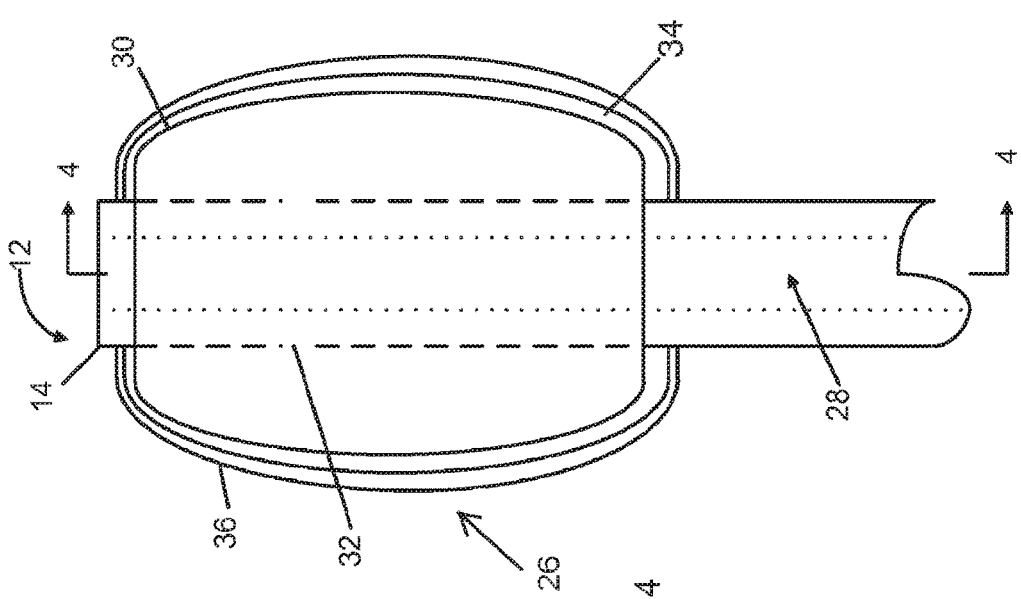
FIG. 3 is a detailed side view, taken along line 2-2 of FIG. 1, of the balloon and cage positioning mechanism of the catheter system of FIG. 1 in a deployed position.

The positioning mechanism 26 of the catheter body 12 shown in FIG. 2 is shown in FIGS. 3 and 4 in a deployed position. As can be seen, the balloon 34 and the cage 36 have been radially expanded to provide for a centered position of the catheter body 12. It can be noted that the balloon 34 and the cage 36 may be expanded when the catheter body is positioned next to an occlusion within a blood vessel, such that the balloon 34 and the cage 36 are placed in contact with an inner surface of the wall of the blood vessel. The expansion of the balloon 34 and the cage 36 may be equidistant around the catheter body 12, such that the catheter body 12 is centered within the blood vessel when the positioning mechanism 26 of the catheter body 12 is in the deployed position.

Figure 6:
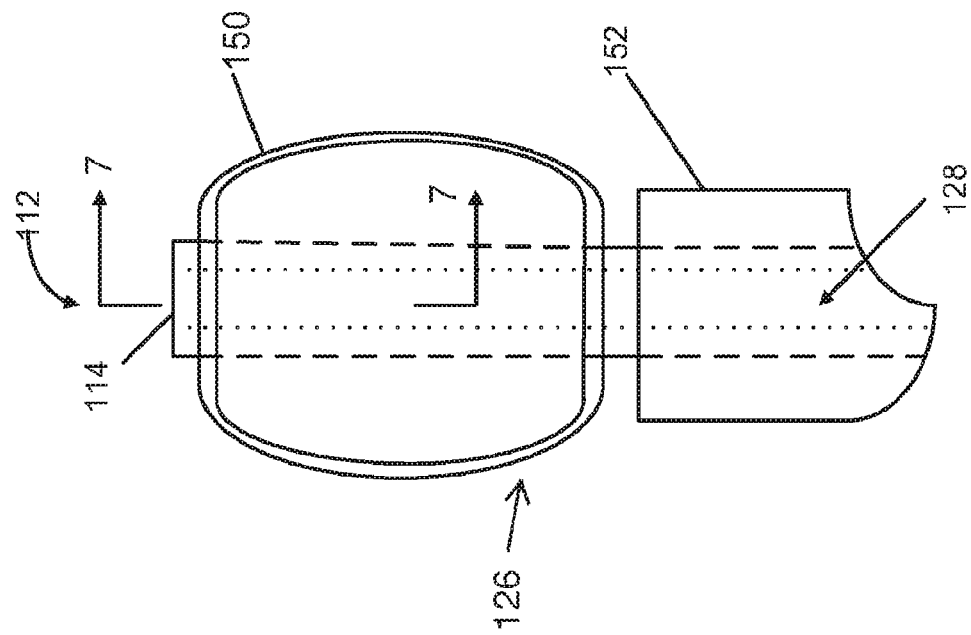
FIG. 6 is a detailed side view, similar to FIG. 3, of the self-expanding cage positioning mechanism of FIG. 5 in a deployed position.
Figure 5:
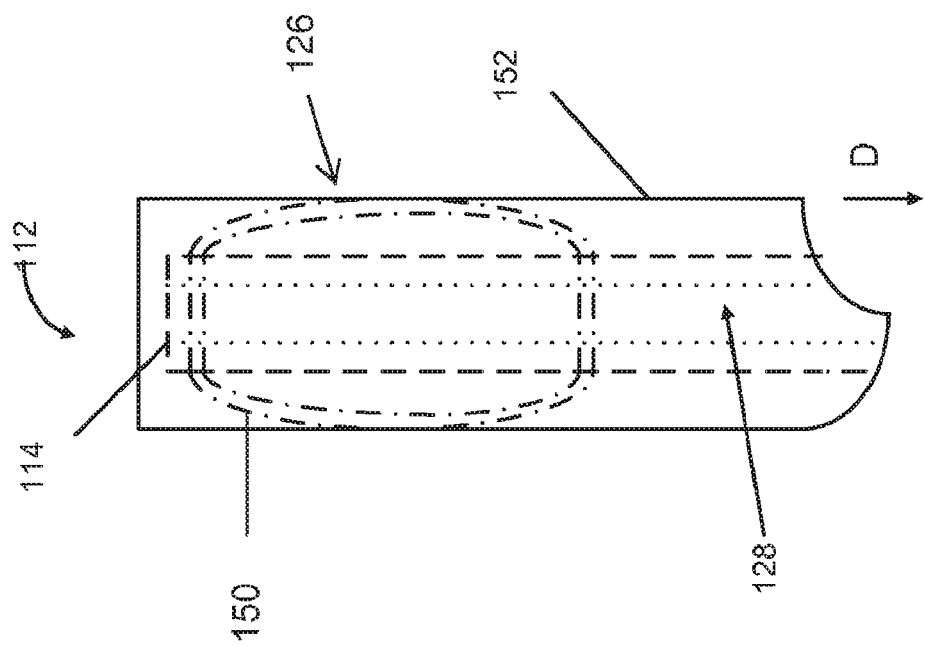
FIG. 5 is a detailed side view, similar to FIG. 2, of another embodiment of a catheter body having a self-expanding cage positioning mechanism in a retracted position.

Another example embodiment of a positioning mechanism 126 of a catheter body 112 is shown in FIGS. 5 and 6. The catheter body 112 includes a lumen 128 configured to receive an elongate object, for example a pilot needle or an ultrasound transmitter. The catheter body 112 further includes a self-expanding cage 150 and a tubular sheath 152 that removably covers the self-expanding cage 150. The self-expanding cage 150 may comprise an elastic metallic or polymeric material. One example material is a superelastic nickel-titanium alloy. The self-expanding cage 150 may take a retracted position when the sheath 152 is covering the cage 150. As can be seen in FIGS. 5 and 6, the cage 152 may be uncovered by retracting the sheath 152 in direction D, causing the self-expanding cage 152 to radially expand into a deployed position of FIG. 7. It may be noted that the self-expanding cage 152 may be deployed when the catheter body 112 is placed next to an occlusion within a blood vessel, such that the self-expanding cage 152 contacts an inner surface of a wall of the blood vessel. The expansion of the self-expanding cage 152 may be equidistant around the catheter body 112, such that the catheter body 112 is centered within the blood vessel when the self-expanding cage 152 is deployed.

Figure 7:
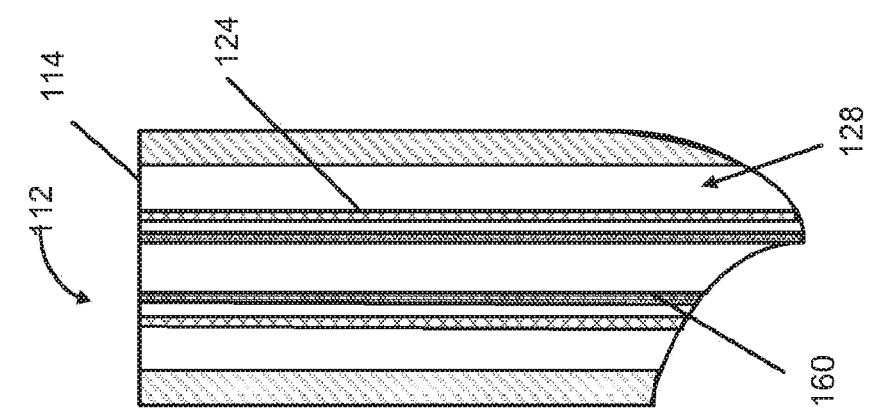
FIG. 7 is a cross sectional view the self-expanding cage positioning mechanism of FIG. 6 taken along line 7-7 of FIG. 6 showing a catheter body having a pilot needle and an ultrasound transmitter disposed within the catheter body.

Looking at FIG. 7, it is possible for the catheter body 112 to include a pilot needle 124 configured to contact the occlusion and to form a pilot hole in the occlusion. As can be seen in FIG. 7, the catheter body 112 may include a lumen 128 configured to receive the pilot needle 124 and an ultrasound transmitter 160. A distal end 114 of the catheter body 112 may be hollow, such that the pilot needle 124 can traverse beyond the distal end 114. In the example embodiment of FIG. 7, the pilot needle 124 is hollow, such that the ultrasound transmitter 160 can be disposed within the pilot needle 124.

Figure 8:
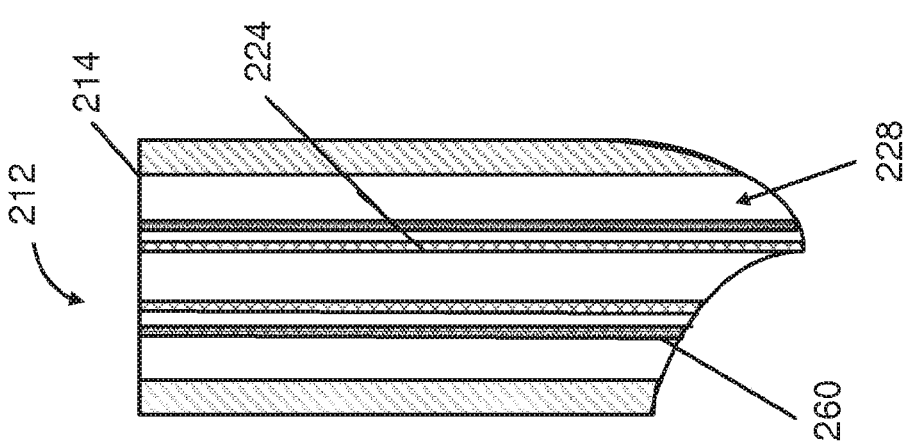
FIG. 8 is a cross sectional view, similar to FIG. 7, of another embodiment of a catheter body having a pilot needle and an ultrasound transmitter disposed within the catheter body.

Another example embodiment of a catheter body 212 can be seen in FIG. 8. The catheter body 212 includes the pilot needle 224, and an ultrasound transmitter 260 disposed within the lumen 228. A distal end 214 of the catheter body 212 is hollow, such that the pilot needle 224 can traverse beyond the distal end 214. In this embodiment, the ultrasound transmitter 260 may be hollow, such that the pilot needle 224 can be disposed within the ultrasound transmitter 260.

Figure 9:
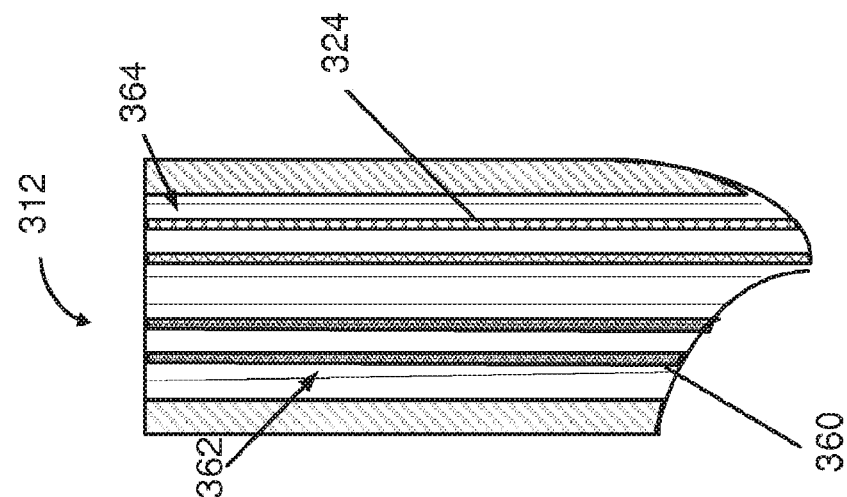
FIG. 9 is a cross sectional view, similar to FIG. 7, of another embodiment of a catheter body having a pilot needle and an ultrasound transmitter disposed within the catheter body.

Another example embodiment of a catheter body 312 can be seen in FIG. 9. The catheter body 312 includes a first lumen 362 and a second lumen 364. An ultrasound transmitter 360 is disposed within the first lumen 362 and the pilot needle 324 is disposed within the second lumen 364. It is also possible for the ultrasound transmitter 360 to be disposed within the second lumen 364 and for the pilot needle 324 to be disposed within the first lumen 362. In one non-limiting form, the pilot needle 324 has an outside diameter of 0.010 inches to 0.040 inches.

The ultrasound catheter system 10 may be used to ablate or disrupt an occlusion within a blood vessel. The ultrasound catheter system 10 may be guided from an access site on a subject's body to a target site within a blood vessel adjacent to the occlusion. The positioning mechanism 26, for example, a balloon, a balloon and a surrounding cage, or a self-expanding cage, may be radially expanded from a first retracted position to a second deployed position to position the catheter body 12 within the blood vessel. A pilot needle 24, or 124, or 224, or 324 may optionally be used to contact the occlusion and to create a pilot hole within the occlusion. The occlusion may also be contacted with the distal end 14 of the ultrasound transmitter 160 or 260 or 360 in the region of the pilot hole, and ultrasonic energy can be applied to the tip of the ultrasound transmitter 160, 260, 360. The ultrasonic energy provides a mechanical vibration at the distal end 14 of the ultrasound transmitter 160, 260, 360 to disrupt the occlusion within the blood vessel.

The present invention has been described in connection with certain embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

What is claimed is:

1. An ultrasound catheter system for disrupting an occlusion within a blood vessel which can be guided from an access site on a subject's body to a target site adjacent to the occlusion, the ultrasound catheter comprising:
   an elongate catheter body having a proximal portion, a distal portion, and a first lumen;
   an ultrasound transmitter extending longitudinally through the first lumen of the catheter body and having a proximal end and a distal end, the distal end configured to provide mechanical vibration from the ultrasound transmitter to disrupt the occlusion within the blood vessel;
   a positioning mechanism located at a distal end of the catheter body, the positioning mechanism having a first retracted position and a second deployed position;
   a pilot needle disposed within the ultrasound transmitter;
   wherein the positioning mechanism is radially expandable from the first retracted position to the second deployed position to position the catheter in the blood vessel,
   wherein the distal end of the ultrasound transmitter is open to the biological environment, and
   wherein the pilot needle is configured to traverse beyond the distal end of the ultrasound transmitter and create a pilot hole within the occlusion prior to the distal end disrupting the occlusion.

2. The ultrasound catheter system of claim 1, wherein the positioning mechanism comprises a balloon.

3. The ultrasound catheter system of claim 2, further comprising an inflation lumen having an outlet in fluid communication with an interior space of the balloon;
   wherein the inflation lumen is configured to provide a fluid from the proximal end of the inflation lumen to the interior space of the balloon; and
   wherein the balloon moves from the retracted position to the deployed position when the fluid enters the interior space of the balloon.

4. The ultrasound catheter system of claim 3, wherein the positioning mechanism further comprises a cage surrounding the balloon.

5. The ultrasound catheter system of claim 1, wherein the positioning mechanism comprises a self-expanding cage.

6. The ultrasound catheter system of claim 5, further comprising a sheath configured to removably cover the cage,
   wherein the cage moves from the retracted position to the deployed position when the sheath uncovers the cage.

7. An ultrasound catheter system for disrupting an occlusion within a blood vessel which can be guided from an access site on a subject's body to a target site adjacent to the occlusion, the ultrasound catheter system comprising:
   an elongate catheter body having a proximal portion, a distal portion, and a first lumen;

an ultrasound transmitter extending longitudinally through the first lumen of the catheter body and having a proximal end and a distal end, the distal end configured to provide mechanical vibration from the ultrasound transmitter to disrupt the occlusion within the blood vessel; and a pilot needle configured to traverse beyond the distal end of the ultrasound transmitter and create a pilot hole within the occlusion prior to the distal end disrupting the occlusion, wherein the pilot needle is hollow, and wherein the ultrasound transmitter extends longitudinally through the pilot needle.

8. The ultrasound catheter system of claim 7, wherein the pilot needle has an outside diameter of 0.010 inches to 0.040 inches.

9. The ultrasound catheter system of claim 7, further comprising a positioning mechanism located at a distal end of the catheter body, the positioning mechanism having a first retracted position and a second deployed position, wherein the positioning mechanism is radially expandable from the first retracted position to the second deployed position to position the catheter in the blood vessel.

10. The ultrasound catheter system of claim 9, wherein the positioning mechanism comprises a self-expanding cage.

11. The ultrasound catheter system of claim 9, wherein the positioning mechanism comprises a balloon.

12. A method for disrupting an occlusion within a blood vessel, the method comprising:
(a) guiding an ultrasound catheter system from an access site on a subject's body to a target site adjacent to the occlusion, the ultrasound catheter system comprising (i) an elongate catheter body having a proximal portion, a distal portion, and a first lumen; (ii) an ultrasound transmitter extending longitudinally through the first lumen of the catheter body and having a proximal end and a distal end; and (iii) a positioning mechanism located at a distal end of the catheter body, the positioning mechanism having a first retracted position and a second deployed position;
(b) radially expanding the positioning mechanism from the first retracted position to the second deployed position to position the catheter in the blood vessel;
(c) contacting the occlusion with the distal end of the ultrasound transmitter; and
(d) applying ultrasonic energy to the ultrasound transmitter to provide mechanical vibration at the distal end of the ultrasound transmitter to disrupt the occlusion within the blood vessel, wherein the step of contacting the occlusion includes creating a pilot hole in the occlusion with a pilot needle that extends through the ultrasound transmitter prior to contacting the occlusion with the distal end.

13. The method of claim 12, wherein the positioning mechanism comprises a balloon.

14. The method of claim 13, wherein the ultrasound catheter system further comprises an inflation lumen having an outlet in fluid communication with an interior space of the balloon;

wherein the inflation lumen is configured to provide a fluid from the proximal end of the inflation lumen to the interior space of the balloon; and wherein the balloon moves from the retracted position to the deployed position when the fluid enters the interior space of the balloon.

15. A method for disrupting an occlusion within a blood vessel, the method comprising:
(a) guiding an ultrasound catheter system from an access site on a subject's body to a target site adjacent to the occlusion, the ultrasound catheter system comprising (i) an elongate catheter body having a proximal portion, a distal portion, and a first lumen; (ii) an ultrasound transmitter extending longitudinally through the first lumen of the catheter body and having a proximal end and a distal end; and (iii) a pilot needle;
(b) creating a pilot hole within the occlusion using the pilot needle;
(c) contacting the pilot hole within the occlusion with the distal end of the ultrasound transmitter; and
(d) applying ultrasonic energy to the ultrasound transmitter to provide mechanical vibration at the distal end of the ultrasound transmitter to disrupt the occlusion within the blood vessel after creating the pilot hole with the pilot needle.

16. The method of claim 15, wherein the ultrasound transmitter is hollow, and wherein the pilot needle extends longitudinally through the ultrasound transmitter.

17. The method of claim 15, wherein the pilot needle is hollow, and wherein the ultrasound transmitter extends longitudinally through the pilot needle.

* * * * *